United States Patent
Demathelin et al.

(10) Patent No.: US 7,881,823 B2
(45) Date of Patent: Feb. 1, 2011

(54) ROBOTIC POSITIONING AND ORIENTATION DEVICE AND NEEDLE HOLDER COMPRISING ONE SUCH DEVICE

(75) Inventors: Michel Demathelin, Strasbourg (FR); Benjamin Maurin, Cran-Gevrier (FR); Bernard Bayle, Strasbourg (FR); Jacques Gangloff, Mulhausen (FR); Olivier Piccin, Mittelhausen (FR)

(73) Assignees: Institut National des Sciences Appliquees, Strasbourg (FR); Institut de Recherche sur les Cancers de l'Appareil Digestif - IRCAD, Strasbourg (FR); Universite Louis Pasteur, Strasbourg (FR); Centre National de la Recherche Scientifique, Paris (FR)

( * ) Notice: Subject to any disclaimer, the term of this patent is extended or adjusted under 35 U.S.C. 154(b) by 764 days.

(21) Appl. No.: 11/663,689

(22) PCT Filed: Sep. 22, 2005

(86) PCT No.: PCT/FR2005/002357

§ 371 (c)(1),
(2), (4) Date: Mar. 23, 2007

(87) PCT Pub. No.: WO2006/035143

PCT Pub. Date: Apr. 6, 2006

(65) Prior Publication Data

US 2009/0143907 A1    Jun. 4, 2009

Related U.S. Application Data

(60) Provisional application No. 60/612,503, filed on Sep. 24, 2004.

(51) Int. Cl.
*G06F 19/00* (2006.01)

(52) U.S. Cl. .................. 700/245; 74/490.01; 74/490.03; 74/490.05; 318/568.1

(58) Field of Classification Search .................. 700/245; 74/490.06, 490.01, 490.03, 490.05; 318/568.1, 318/568.2, 568.21; 606/130
See application file for complete search history.

(56) References Cited

U.S. PATENT DOCUMENTS 5,752,834 A * 5/1998 Ling ............................ 434/58

(Continued)

OTHER PUBLICATIONS

B. Maurin et al., "A new robotic system for CT-guided percutaneous procedures with haptic feedback", Jun. 26, 2004, Elsevier B.V., Proceedings of the 18th International Congress and Exhibition (CARS 2004), pp. 515-520.*

(Continued)

*Primary Examiner*—Khoi Tran
*Assistant Examiner*—Stephen Holwerda
(74) *Attorney, Agent, or Firm*—Fay Sharpe LLP

(57) ABSTRACT

The invention relates to a robotic device for the positioning and orientation of a platform that is connected thereto by means of articulated support structures forming parallel mechanical links, each in the form of a serial kinematic chain of articulations that are interconnected by support segments. The inventive device (1) is characterized in that it comprises three articulated parallel mechanical links comprising: (i) two opposing, symmetrical and co-planar support structures (4 and 5), and (ii) a third support structure (6) which is located in a plane that is perpendicular to the plane containing the support structures (4 and 5). According to the invention, the articulated links formed by the three supports structures (4, 5 and 6) enable the controlled movement of points belonging to the platform (2) on a surface corresponding to a spherical or ellipsoidal cap and, preferably, essentially to a half-sphere, thereby providing at least five degrees of freedom.

32 Claims, 19 Drawing Sheets

U.S. PATENT DOCUMENTS

| | | | | |
|---|---|---|---|---|
| 6,116,844 | A | 9/2000 | Hayward et al. | 414/680 |
| 6,135,683 | A * | 10/2000 | Kim et al. | 409/132 |
| 6,196,081 | B1 * | 3/2001 | Yau | 74/479.01 |
| 6,330,837 | B1 * | 12/2001 | Charles et al. | 74/490.06 |
| 6,418,811 | B1 * | 7/2002 | Rosheim | 74/490.06 |
| 6,516,681 | B1 * | 2/2003 | Pierrot et al. | 74/490.01 |
| 2002/0133174 | A1 * | 9/2002 | Charles et al. | 606/130 |
| 2003/0070311 | A1 * | 4/2003 | Zhu et al. | 33/502 |
| 2004/0144288 | A1 * | 7/2004 | Chiang | 108/1 |
| 2004/0146388 | A1 * | 7/2004 | Khajepour et al. | 414/680 |
| 2004/0246494 | A1 * | 12/2004 | Li et al. | 356/601 |

OTHER PUBLICATIONS

B. Maurin et al., "A Parallel Robotic System with Force Sensors for Percutaneous Procedures Under CT-Guidance", Sep. 23, 2004, SpringerLink, Medical Image Computing and Computer-Assisted Intervention—MICCAI 2004, pp. 176-183.*

Maurin, et al. "A New Robotic System for CT-Guided Percutaneous Procedures with Haptic Feedback", Int'l Congress Series, CARS 2004, V. 1268, Jun. 2004, pp. 515-520 XP002364083.

Schreiber, et al. "Analyse et Conception d'un Manipulateur Parallèle Spatial á Cinq Degrés de Liberté", Mech Mach Theory, V. 38, N. 6, Jun. 2003, pp. 535-548 XP002364084.

Maurin, et al. "Pose Reconstruction with an Uncalibrated Computed Tomography Imaging Device", Proc. of 2003 IEEE Comput Sco Conf Comput Vision Pattern Recog 2003, V. 1, 2003 pp. I/455-I460 XP002364805.

Fang, et al., "Structure Synthesis of a Class of 4-DoF and 5-DoF Parallel Manipulators with Identical Limb Structures", Int Journ. Robotics Res., V. 21, No. 9, Sep. 2002, pp. 799-810 XP002364086.

Liu, et al., "Some New Parallel Mechanisms Containing the Planar Four-Bar Parallelogram", Int. Journ. Robotics Res., V. 22, No. 9, Sep. 2002, pp. 717-732 XP008058791.

Maurin, et al., "A Parallel 5 DOF Positioner for Semi-Spherical Workspaces", Proc. ASME Des. Eng. Tech. Conf. 2004, V. 2, 2004, pp. 1033-1042 XP008058750.

* cited by examiner

ROBOTIC POSITIONING AND ORIENTATION DEVICE AND NEEDLE HOLDER COMPRISING ONE SUCH DEVICE

The present invention relates to the field of the robotized devices, in particular the robots for manipulating and/or positioning intended to be used in applications requiring a high degree of precision and a elevated operational safety, for example in the context of medical or surgical interventions.

More specifically, the invention has as an aim a robotic device for positioning and orientating of a platform or the like, as well as a needle-carrying apparatus integral with a robotic device.

In many fields, there is a demand for robust precision robotic devices, of small size and having a sufficient number of degrees of freedom, making it possible to replace a human operator or manipulator by having the same possibilities of movement and the same dexterity as the latter.

Such robotic devices can function in autonomous manner and entirely automatic (for example after a phase of programming and/or preliminary training of a data-processing and control unit), in a semi-automatic way (certain phases or operations being controlled by an operator, possibly with the assistance of a data-processing unit) or while being directly controlled by an operator by means of an adaptive interface (with direct visual monitoring or by camera/monitor and with or without feedback).

The need for such robotized devices is particularly pressing in work environments that are noxious or harmful to humans.

In the medical field, for example, one finds such environmental conditions within the environment of x-ray image guided surgery, in particular for the minimally invasive procedures which are a growing success because of a faster recovery of the patient and a less pain caused during the surgery.

The precision needed in these procedures is such that they need to carry-out the procedure in the field of an x-ray diagnostic imaging device, such as for example a computerized tomographic scanner (better known under the designation "CT scan"). In this manner, the practitioner is exposed to a significant and cumulative amount of radiation which is harmful for his health.

To try to rectify this acutely risky situation, it was proposed to utilize robotized operational assistants, controlled remotely by the practitioners located out of the irradiation zone.

However, these known robotized assistants do not give satisfaction. Indeed, they are configured as devices which rest on the ground or are fixed on the table which receives the patient and slidingly translates in the examination volume of the scanner. Accordingly, these known robotized devices cannot follow the respiratory movements of the patient and are not suited, in the field of the minimally invasive surgery, with operations in the abdominal region.

In addition, by the means of the various known techniques of medical imaging, it is currently possible to carry out an automatic virtual three-dimensional reconstruction of at least an region of a patient.

On the basis of these data, it is possible for the surgeon to precisely plan the surgery to be carried out and to possibly dispose, during the operation, the superposition of the reconstructed three-dimensional image on the patient, thus rendering the patient virtually transparent.

The development of a device robotic sufficiently precise and reliable, and compatible with the above mentioned environment, could make it possible to lead to an automation of the movements most difficult to carry out.

Thus, the general problem addressed by the present invention includes proposing a robotic device with a high degree of accuracy, of small size, being able to be built starting from simple, robust and reliable components and presenting great flexibility and a great number of possibilities in terms of positioning and movement.

Preferably, and in particular within the framework of a medical application, the robotic device according to the invention will have to be able to be placed on a patient, to be ready to position in a very precise way an elongated object relative to a given point on a surface, to be adapted to move in a small volume (typically free volume remaining in a bore of a scanner) and to be compatible with an environment which is subjected to x-rays.

In order to respond to at least the above mentioned general problem, the invention has as an object a robotic device for positioning and orienting a platform, or a similar support element or the like, having a coordinate system and movable relative to a base support having a coordinate system, the platform being located a distance from, preferably above, the base plate and being connected to the latter by first; second and third articulated leg structures forming three mechanical connections in parallel, each of which includes a series of leg segments or portions of connected together, in pairs, by joints each defining at least one pivot axes, the opposite end portions of each of the three leg structures moreover being connected by joints with at least one pivot axis with the platform and the base plate in predetermined connection points, device characterized in that pivoting axes of the joints of the first and second leg structures with the platform, on the one hand, and the base plate, on the other hand, are are configured in a manner to define a first common axis of rotation between the base plate and the two opposite leg structures and a second common axis of rotation between these last and the platform, in that said common pivot axes are coplanar in a plane, in that the pivot axes of the pivoting joint connecting the leg segments of these two leg structures are all parallel to each other and perpendicular to a given plane, in that the two above mentioned planes are not mutually perpendicular, in that the third articulated leg structure is connected, in an articulated manner, on the one hand, with the platform at a connection point not aligned with the connection points of the two other leg structures with said platform and, on the other hand, with the base plate at a connection point not aligned with the connection points with said base plate of the two other leg structures, the parallel rotary joints provided by these three leg structures permitting a controlled determination of the position of the origin of the coordinate system assigned to the platform and the orientation of the latter coordinate system relative to the coordinate system assigned to the base plate, such that at least five degrees of freedom are provided.

The invention will be better understood thanks to the description hereafter, which is referred to as a preferred embodiment, given by way of nonrestrictive example, and explained with reference to the annexed diagrammatic drawings, in which.

Figure 1:
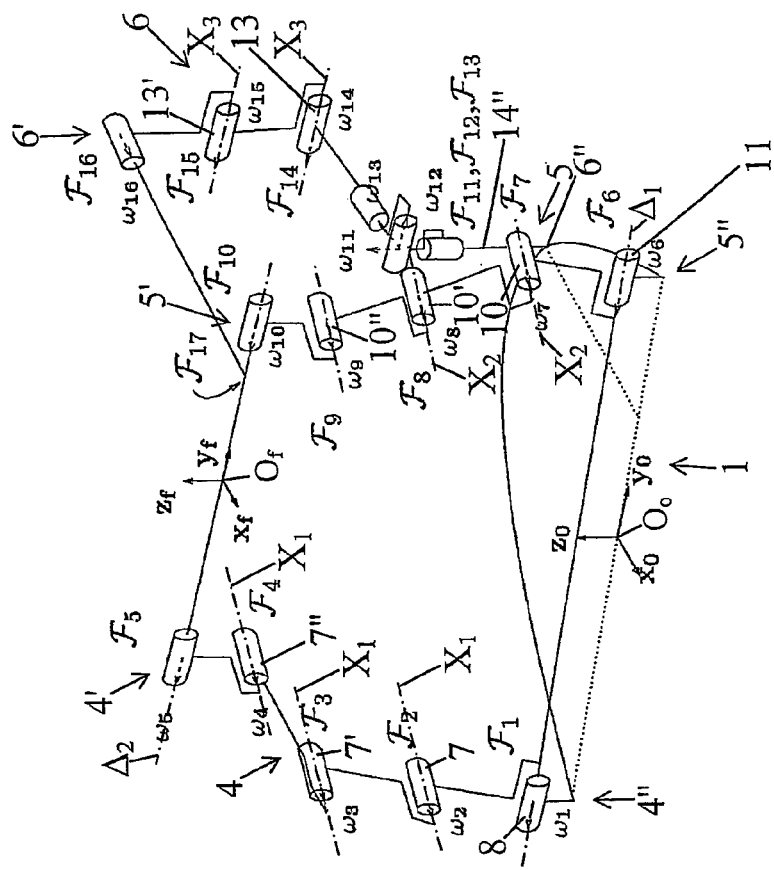
FIG. 1 is a functional diagrammatic representation based on a modeling of the robotic device according to the invention.

The figures of the annexed drawings illustrate, in a diagrammatic way (FIGS. 1 to 4) or in the form of a possible practical embodiment (FIGS. 5 to 20), a robotic device 1 for positioning and orientating a platform 2, a similar support element or the like, provided with a coordinate system $O_f$, $x_f$, $y_f$, $z_f$ and movable relative to a base plate of support 3 provided with a coordinate system $O_0$, $x_0$, $y_0$, $z_0$, the platform being located displaced from, preferably above, the base plate and being connected to the latter by first, second and third articulated leg structures 4, 5, and 6 forming three mechanical links in parallel, of which each one consists of a series of leg segments or portions (for leg 4: 9, 9', 9", 9'" or 9, 24, 9'"/for leg 5: 12, 12', 12", 12'" or 12, 25, 12'"/for leg 6: 15, 15', 15" or 26, 15"). These segments or portions are connected together, in pairs, by the joints each one presenting at least a pivot pin (7, 7', 7" or 7, 7" for leg 4; 10, 10', 10" or 10, 10" for leg 5; 13, 13' or 13' for the leg 6), the opposite end portions of each three leg structures moreover being connected by joints having at least a pivot pin 8', 11', 14'; 8, 11, 14 with the platform 2 and the base plate 3 in determined connection points 4', 5', 6'; 4", 5", 6".

In accordance with the invention, it is envisaged:

that respective pivot pins of the pivoting joint 8', 11'; 8, 11 of the first and second leg structures 4 and 5 with platform 2, on the one part, and the base plate 3, on the other part, are configured in a manner to define a first common axis of rotation $\Delta_1$ between base plate 3 and the two opposite leg structures 4 and 5 and a second common axis of rotation $\Delta_2$ between these last and platform 2, that said common pivot axes $\Delta_1$ and $\Delta_2$ are coplanar in a plane P, that the pivot axes $X_1$; $X_2$ of the pivotal joints 7, 7', 7'" or 7, 7"; 10, 10', 10" or 10, 10" connecting the leg segments 9, 9', 9", 9'" or 9, 24, 9'"; 12, 12', 12", 12'" or 12, 25, 12'" of these two leg structures 4; 5 all are parallel between them and perpendicular to a plane denoted P', in that the two above mentioned planes P and P' are not mutually perpendicular, in that the third articulated leg structure 6 is connected, in a pivotal way, on the one hand, with the platform 2 at a connection point 6' not aligned with the connection points 4', 5' of the two other leg structures 4 and 5 with said platform 2 and, on the other hand, with the base plate 3 in a connection point 6" not aligned with the connection points 4", 5" of the other two leg structures 4 and 5 with said base plate 3, parallel pivotal joints provided by these three leg structures 4, 5 and 6 permitting a controlled setting of the position of the origin $O_f$ the coordinate system, $O_f$, $x_f$, $y_f$, $x_f$ attached to the platform 2 and of the orientation of the latter coordinate system relative to the coordinate system $O_0$, $x_0$, $y_0$, $z_0$ attached to the base plate, this providing at least five degrees of freedom.

According to a first alternate embodiment of the invention, arising from FIGS. 1 to 20 of the annexed drawings, each one of the first and second leg structures 4 and 5 is composed, by observing it in its extension of the base plate 3 towards the platform 2, of four leg segments 9, 9', 9", 9'"; 12, 12', 12", 12'" assembled in series, successively from the first to the fourth, and connected to each other, in pairs, by three joints (7, 7', 7"; 10, 10', 10") pivoting around axes $X_1$; $X_2$ perpendicular to the plane P'.

In a preferred way, a first 4 of the two opposite leg structures 4, 5 comprises two pivoting joints 7' and 7" with requested and controlled movements, preferably the joint 7' connecting the second and third segments 9' and 9" on the one part and the joint 7" connecting the third and fourth segments 9" and 9'" on the other part, and the second 5 of the two opposite legs structures 4 and 5 comprises a single pivoting joint 10' with controlled and requested movement, preferably joint 10' connecting the second and third segments 12' and 12" (other pivoting joints 7, 10 and 10" being with free movement).

Figure 4:
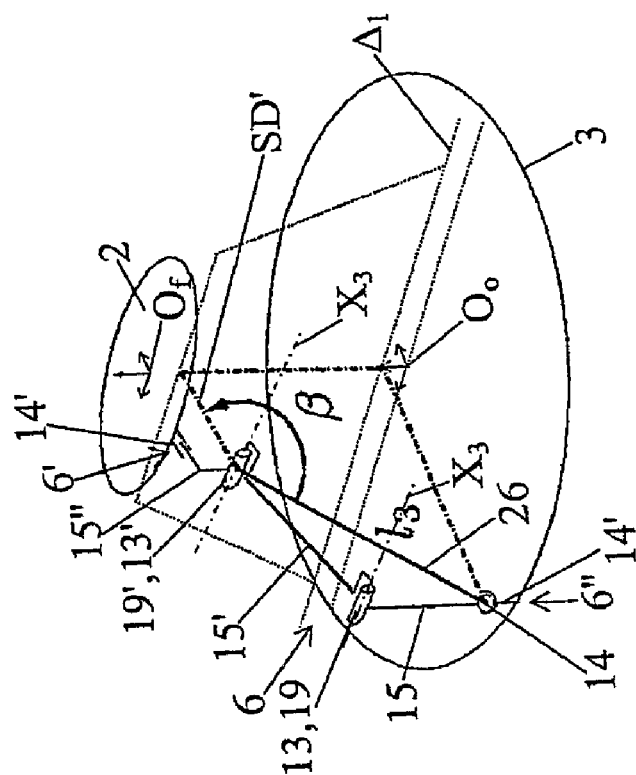
FIGS. 3 and 4 are skeletal or linkage diagrammatic representations of two alternate embodiments, respectively, of the first two opposite leg structures and a third leg structure, also showing the controlled parameters and controls on the level of each one of these structures.
Figure 3:
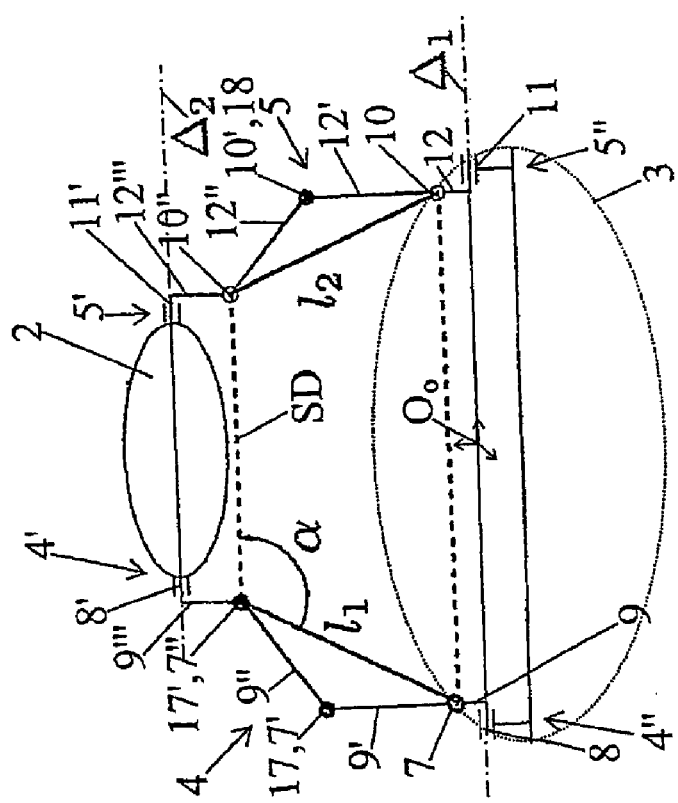

According to a second alternate embodiment of the invention, represented in a superimposed manner with the first alternative on FIGS. 3 and 4 (the segments 24; 25 having to be regarded as construction alternatives respectively relative to the pairs of segments 9', 9"; 12', 12"), each one of the first and second leg structures 4 and 5 are composed, it is seen in its extension from the base plate 3 towards the platform 2, of three leg segments 9, 24, 9'"; 12, 25; 12'" assembled in series, successively the first to the third, and connected to each other, in pairs, by two pivoting joints 7, 7"; 10, 10" around axes $X_1$; $X_2$ perpendiculars in the plane P' and in that the leg segments 24 and 25 includes telescoping segments.

In relation to this second embodiment, it can then advantageously be expected that the two telescoping segments 24 and 25 are adjustable in length in a controlled way, and that one of the pivoting joints 7, 7"; 12, 12" of the one of the first and second leg structures 4; 5 is ordered and controlled in movement (for example joint 7", other pivoting joints being free moving).

Thus, according to the classification suggested by L. W. TSAI in "Mechanism Design: enumeration of kinematic structures according to function" (Design of mechanisms: enumeration of kinematic structures in accordance with their function); Mechanical Engineering Series; CRC Press; 2001, the two opposite leg structures 4 and 5 in the form of parallel chains form a connection plane with six bars. This connection aims at controlling three degrees of freedom in its plane, namely, the position of the point origin $O_f$ the coordinate system attached to the platform 2 and the orientation of the second axis of rotation $\Delta_2$ in the plane of the complex connection formed by the two leg structures 4 and 5.

For reasons of simplicity of construction and optimization of movement, the planes P and P' are advantageously parallel, preferably configured. In this case, the axes of rotation or pivoting $X_1$ and $X_2$ are all perpendicular to the plane P containing the mechanical connection axes of the leg segments 4 and 5.

According to a very advantageous embodiment of the invention, arising in particular from FIGS. 1 to 3 and 6 to 12, the first and second leg structures 4 and 5 constitute opposite and symmetrical leg structures, with pivoting joints 7, 7', 7" or 7, 7'''; 10, 10', 10" or 10, 10''' respectively located in a symmetrical manner and the leg segments 9, 9', 9", 9''' or 9, 24, 9'''; 12, 12', 12", 12''' or 12, 25, 12''' of identical forms respectively, the longitudinal axes of all the above mentioned leg segments, or at least axes of the direct mechanical connections respectively provided by the latter, being located in the plane P and/or the plane P', or in a plane parallel to one of these two planes. Thus, the two leg structures 4 and 5 present a completely symmetrical structure in terms of mechanical construction and facility for pivoting.

As shows in FIG. 3 of the annexed drawings, the drive for the pivoting joints 7', 7" and 10' is effected in such a way that the two mechanical connections and parallel kinematics formed by the first and second opposite leg structures 4 and 5 connecting the base plate 3 to the platform 2 include three controlled parameters, namely, on the one part, on the level of the first 4 of the two leg structures 4 and 5, the distance l1 between the axis $X_1$ of the pivoting joint 7 connecting the first and the second leg segments 9 and 9' and the axis $X_1$ of the pivoting joint 7" connecting the third and the fourth leg structures 9" and 9''', and, the angle α between the straight segment connecting two joints 7 and 7" above mentioned and defining the length l1 and the straight line segment SD connecting last 7" of the above mentioned joints of the first leg structure 4 to the corresponding joint 10" of the second leg structure 5, and, in addition, on the level of the second 5 of the two leg structures 4 and 5, the distance l2 between the axis $X_2$ of the joint 10 connecting the first and the second leg segments 12 and 12' and the axis $X_2$ of joint 10" connecting the third and fourth leg segments 12" and 12'''.

Figure 2:
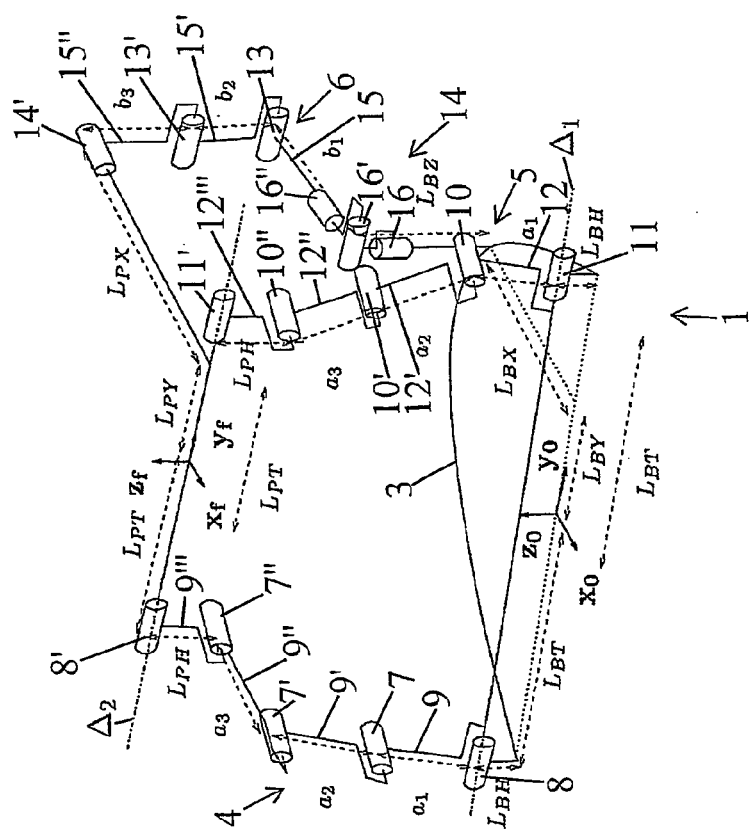
FIG. 2 is a kinematic diagrammatic representation based on same modeling of the robotic device as that of FIG. 1.

In order to shift the third leg structure 6 out of the median plane, and if need be the plane of symmetry, of the first and second leg structures 4 and 5, so as to limit the observed interference on the level of this plane with the selected probe, it can advantageously, be expected that the connection point 6' of the third leg structure 6 with platform 2 is located apart from the median plane $O_f$, $x_f$, $z_f$ of the two other connection points 4' and 5' of said platform 2, perpendicular to the axis of rotation $\Delta_2$, and that the connection point 6" of the third leg structure 6 with the base plate 3 is located apart from the median plane $O_0$, $x_0$, $z_0$ of the two other connection points 4" and 5" of said platform 2, perpendicular to the axis of $\Delta_1$ rotation (see in particular FIGS. 1 and 2).

Similarly with the two alternate embodiments illustrated above relative to the principles of the first and second leg structures 4 and 5, two similar alternate embodiments can be envisioned for the third leg structure 6.

Thus, according to a first alternative, arising from FIGS. 1 to 20, the third leg structure 6 is composed, as seen in its extension from the base plate 3 towards platform 2, of three leg segments 15, 15', 15" assembled in series successively from the first to the third, and connected to each other, in pairs, by two pivoting joints 13 and 13' around the parallel axes $X_3$.

According to a second alternative, represented in a superimposed manner with the first alternative on FIG. 4 (the segment 26 having to be regarded as an alternate construction to replace segments 15 and 15'), the third leg structure 6 is composed, it is seen in its extension from the base plate 3 towards the platform 2, of two leg segments 26, 15" assembled together by an pivoting joint 13' around an axis $X_3$, one 26 of the two leg segments 26, 15" being of a telescopic type.

For reasons of simplicity of construction and optimization of movement, it can be expected that the longitudinal axes of the leg segments 15, 15', 15" or 26, 15", or at least the axes of the right (straight, upright) mechanical connections respectively provided by the latter, can be located in one or more perpendicular plane(s) to the pivot axis or axes $X_3$.

In an advantageous manner, and as arises from the figures of the annexed drawings, the opposite end leg segments 15 and 15" of the third leg structure 6 are, each, connected by a free joint 14, 14' respectively with the base plate 3 and the platform 2. Preferably, the joint 14 connecting the first segment 15 to the base plate 3 is of the knee type and the joint 14' connecting the third segment 15" to platform 2 is of the type to pivot around an axis perpendicular to the pivot axis $\Delta_2$.

Thus, this third leg structure 6 can be considered, according to above mentioned classification, likewise comprises a four bar linkage connected by a six bar linkage to a platform 2.

This four bar connection defines the two remaining degrees of freedom of device 1, namely, the position of the origin $O_f$ around a circle contained in a plane normal to the axis $\Delta_1$ (rotation of the planar six bar connection around the axis $\Delta_1$), and the orientation of the vector $z_f$ around the axis $\Delta_2$ (rotation of the platform around $\Delta_2$).

In accordance with another advantageous characteristic of the invention, the mechanical and kinematic connection formed by the third leg structure 6 includes two controlled parameters, namely, the distance l3 between the center of the free knee joint 14 and the axis $X_3$ of the pivoting joint 13' connecting the first and the second leg segments 26, 15" or the second and the third leg segments 15' and 15" and the angle β between the straight line connecting the two preceding joints 14 and 13' and defining the distance l3 and a straight line SD' contained in the plan containing said straight line defining the l3 distance containing the longitudinal axes of the leg segment 15, 15', 15" or 26, 15" and/or corresponding mechanical connections and connecting the axis $X_3$ of the above mentioned pivoting joint 13' to the straight line SD connecting the pivoting joints 7" and 10" of the first and second leg structures 4 and 5.

In accordance with the two alternate embodiments of the third leg structure 6 evoked previously, it can respectively be expected that the two pivoting joints 13 and 13' are both driven and controlled in movement, or that the pivoting joint 13' are driven and controlled in movement, with the telescopic leg segment 26 adjustable in length in a controlled way.

Advantageously, all the pivoting or rotating joints 7, 7', 7", 8, 8', 10, 10', 10", 11, 11', 13, 13', 14, 14' are made of cylindrical joints (for example ball or needle bearings) and the knee joint 14 can be made of the juxtaposed association of three pivoting or rotating l joints 6, 16', 16" comprising axes of concurrent rotation or pivoting.

The distance separating the joint 14 from the plane containing the base plate 3 can optionally be adjustable, for example by a telescopic connecting segment 14" between this joint and the base plate 3.

By using the mathematical notations arising from FIGS. 3 and 4, it is possible to model the robotic device 1 according to the preferred embodiment of the invention while being based on the methods disclosed in the following publications:

"A Mathematical Introduction to Robotic Manipulation" (A mathematical introduction to robotic manipulation), Murray, R. M., Li Z, Sastry S. S., 1994, CRC Press.

"Computational aspects of the product-of-exponentials formula for robot kinematics" (Computational aspects of the product-of-exponentials formula for robot kinematics), Park, F C, 1994, IEEE Transactions one Automatic Control, 39 (3) March, pages 643-647.

Design and kinematic analysis of modular reconfigurable parallel robots" (Design and kinematic analysis of modular reconfigurable parallel robots), Yang, G, Chen I Mr., Lim, W K, Yeo, S. H., 1999, Proceedings of the 1999 IEEE International Conference one Robotics and Automation, pages 2501-2506.

A kinematic modeling of the robotic device 1 object of the invention is developed and described in the following document:

"A PARALLEL 5 DOF POSITIONER FOR SEMI-SPHERICAL WORKSPACES" (Parallel positioner with 5 degrees of freedom for semi-spherical workspaces); Maurin B. et al., Proceedings of DETC '04, Design Technical Engineering Conferences, Salt Lake City, USA, Sep. 28, 2004, ASME, 2004.

As is disclosed by this last document, whose contents are incorporated by reference into present application, the formalism of the local product of exponential as described in the above mentioned publications is used to simulate the kinematics of the robotic device 1 and one Jacobian matrix numerical approximation is used to study the workspace and the rigidity of the mechanism formed by the parallel articulated leg structures 4, 5 and 6.

When the robotic device 1 is implemented in the examination volume of a scanner, it can advantageously be expected that none the constituent elements of the each of the three leg structures 4, 5 and 6 is not located in the scan plane of the aforesaid scanner (plane perpendicular to the central axis of the examination volume of the scanner or in the plane of symmetry of the patient).

In accordance with a practical preferred embodiment of the invention, applied to the first preceding alternative, the actuators 17, 17'; 18; 19, 19' drive and control the movements respectively of the joints 7', 7"; 10'; 13, 13' driving and controlling movement of the three leg structures 4, 5 and 6 are composed of piezoelectric or ultrasonic driving assemblies.

In relation to the second above mentioned alternative, it can be expected that the telescopic leg segments 24, 25, 26 are composed of electric or piezoelectric extension cylinders and that the pivoting joints 7''', 13' in driven and controlled movement are composed of piezoelectric or ultrasonic driving assemblies 17', 19'.

More precisely each one of the driving assemblies 17, 17', 18, 19 and 19' (each one providing respectively with the one of the pivoting joints with controlled movement 7', 7", 10', 13, 13') can include an ultrasonic or piezoelectric motor associated a reducer, preferably with a harmonic drive ("harmonic drive" in the English language), and with an position coder, each one of these assemblies being mounted in a corresponding housing and controlled in accordance with the other assemblies by a central command and control unit, such as a programmable data-processing unit, which receives the data delivered by the various encoders.

This type of driving assembly is particularly well adapted to a use within the framework of the invention. Indeed, the ultrasonic drives present a high torque maintenance, a high torque/load ratio, a low response time, a low dynamic response, a good magnetic compatibility and no play or hysteresis. The implemented driving assemblies can for example be of the type known under designation USR-30 by the Shinsei Company, available with suitable control units with integrated power amplifiers. An angular control of the driving sets can be carried out by a loop control between the encoders and said control units associated with each one of the aforesaid driving assemblies.

Of course, the operation and the control of the latter will be carried out by a data-processing unit 21 on the basis of the data provided by the encoders and by an imaging system 22 in real time.

In order to reduce the disturbances induced by the robotic device 1 on the images as much as possible, the various leg segments 9, 9', 9", 9''', 12, 12', 12", 12''', 15, 15', 15", 24, 25, 26, as well as the platform 2 and the base plate 3, are made out of a rigid material and compatible with medical imaging processes, in particular of the type with x-rays, such as for example glass fiber reinforced polyamide, and the pivoting joints 7, 7', 7", 8', 10, 10', 10''', 11, 11', 13, 13' of the three leg structures 4, 5, 6 are made of cylindrical or annular bearings.

In order to allow a permanent and precise space localization of the robotic device 1 by a medical imaging system 22, said device 1 comprises moreover at least a spatial reference and multiaxial indexing piece 1', for example in the form of a cube of a plastic material and containing x-rays opaque markers (for example in a metallic material), carried preferably at the level of the base plate 3 or the housing up to the level of the platform 2.

Such reference pieces 24 for example are described by R. A. Bronn et al., in "Stereotactic frame and computer software for CT-directed neurosurgical localization" (Stereotactic frame and computer software for CT-directed neurosurgical localization), Invest. Radiol., vol. 15, pages 308-312, 1980.

In a particularly advantageous application of the invention, the platform 2 comprises one or more mounting and attachment sites 2' for a device 23 for retaining and axial displacement and controlled depression of a needle or a similar elongated object and/or a device for generating a jet or a linear beam, such as for example a laser, and the base plate 3 presents an appreciably annular form with a central opening 3' located under the platform 2 and of the side extensions 3" forming the feet or a support framework.

These mounting and attachment sites 2' can for example include indexing sockets, indented accommodations, threaded bores for receiving bolts or the like and/or surface configurations of complementary form to that of the device 23 to be mounted and attached.

Such a device 23 for retention and controlled displacement, for example of a needle, in particular is described and represented in the French patent application No. 05 02016 of Feb. 28, 2005.

The side extensions 3" will be able, for example, to extend towards the outside, starting from the central annular body of the base plate 3, on the level of the three joint anchoring points of the three leg structures 4, 5 and 6. A foot 3" or a part of the support framework will be able moreover to include a receiving and attaching structure for the referencing and indexing part 24.

Figure 20:
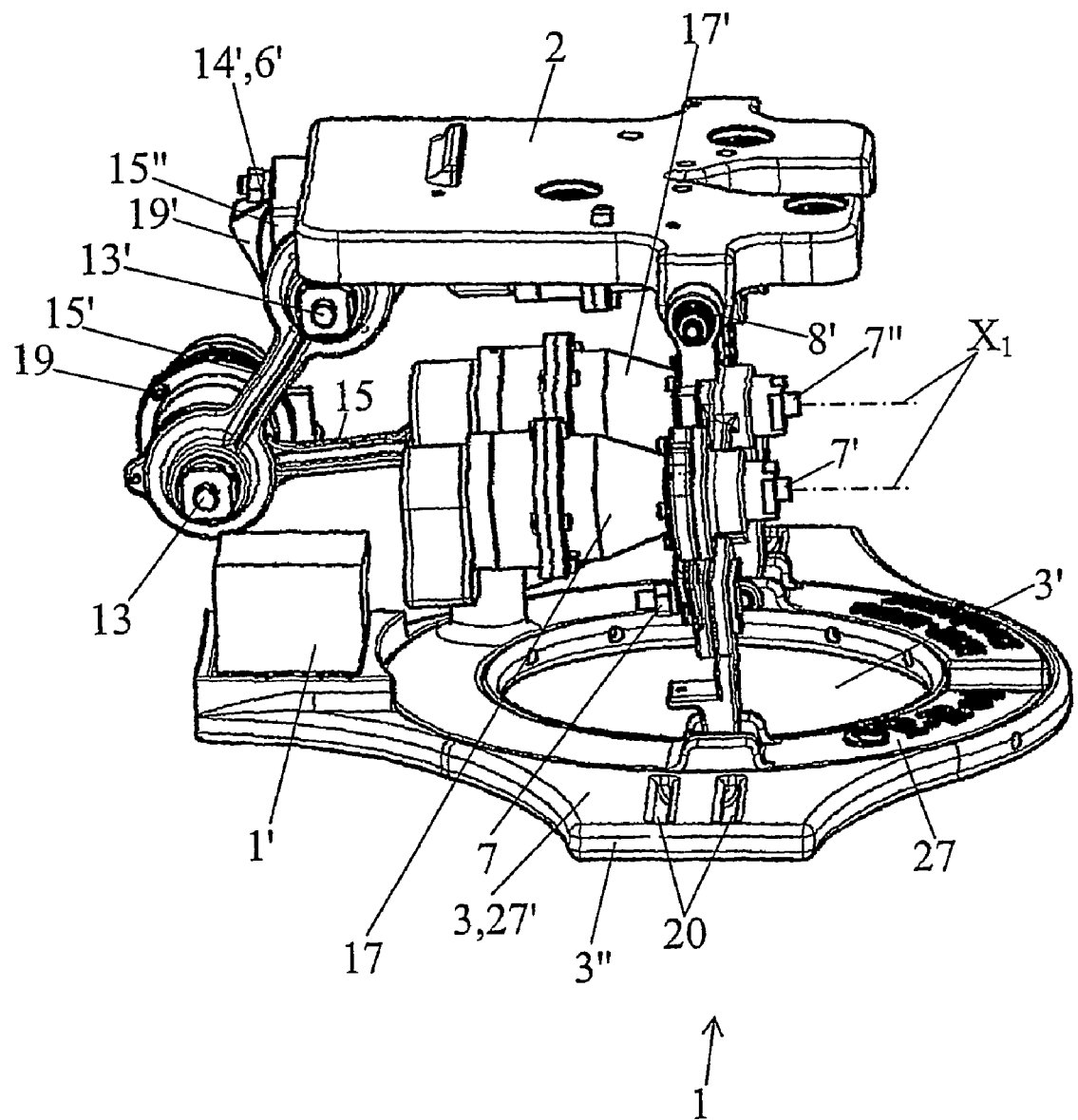
FIG. 20 is a view similar to that of FIG. 8 of a robotic device according to the invention, equipped with a base plate according to another alternate embodiment (identical to that of the device of FIG. 7); and, FIG. 21 is a diagrammatic representation of a needle carrying apparatus including a robotic device according to the invention and implemented in conjunction with a medical imaging system.

According to an alternate embodiment represented on FIG. 20, and to allow an close application and sure and fixed constraint of the robotic device 1 on the trunk or the abdomen of a patient, the base plate 3 can equipped with passage means 20 and/or a fixed receiver, such as slits, grooves or the like, for attachment bands or straps (not represented), permitting an assured positioning of the device 1 on the trunk or the abdomen of a human or animal subject, living or not. Preferably, the slits 20 are also arranged on the opposite support feet 3" extending laterally from the base plate 3 on the level of the lower parts of the first two opposite leg structures 4 and 5.

Within the framework of applications for the device 1 applying of the conditions of sterility and asepsis of an elevated level, such as in the surgical environment, it is imperative that device 1 in its entirety answers the requisite criteria.

A first solution can consist in systematically subjecting, between two consecutive uses, the whole of the device 1 to a sterilizing treatment. This solution accelerates however the ageing of various components, in particular of the joints and the actuators.

One second solution can consist in surrounding device 1 in its totality (inclusively if necessary the device 23 for retention and displacement of the needle) in an envelope which maintains a sterile environment around of the aforesaid device. Nevertheless such a solution does not permit an intimate application, nor an easy assured mounting of the aforesaid device on the body of a patient, for example.

A third solution can consist in disassembling the device 1 into a first single use part of low cost (which contacts the patient 29) and a second reusable part surrounded of an envelope providing a sterile environment.

In accordance with this third solution, the base plate 3 can made of two assembled parts in a removable manner with indexing in rotation around its central opening 3', namely a first part 27 in the form of ring connected to the leg structures 4, 5, 6 and one second part 27' defining the central opening 3', integral with the side extensions 3" and comprising, around said opening 3', a circular groove 27" for the reception of first annular part 27 (the second part 27' being then a single use part).

In order to be able to provide a stable positioning and an intimate contact between the base plate 3 and the body on which the device 1 rests, said base plate 3, if present the second constituent part 27', is provided on its face intended to rest on a support body 29, in particular a human patient, a padding 28 or an equivalent sheathing which adapts to conform to the aforesaid support body by taking on its form, this complementary form being contingently fixed after adaptation.

Figure 5:
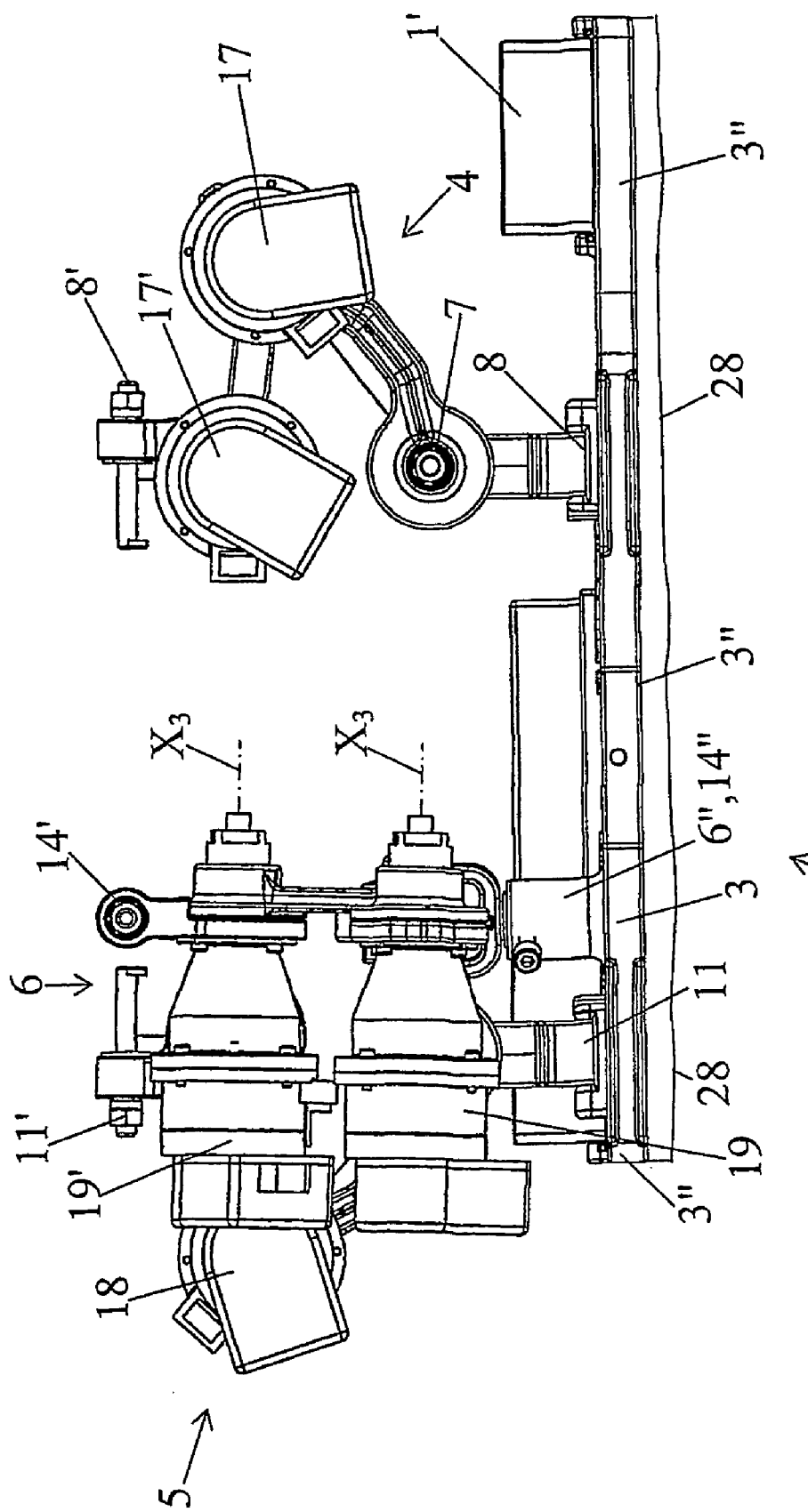
FIGS. 5 and 6 are respectively a side elevational view in a perpendicular direction to the planes of the two opposite leg structure and a top view of the robotic device according to the invention, the platform being removed.
Figure 6:
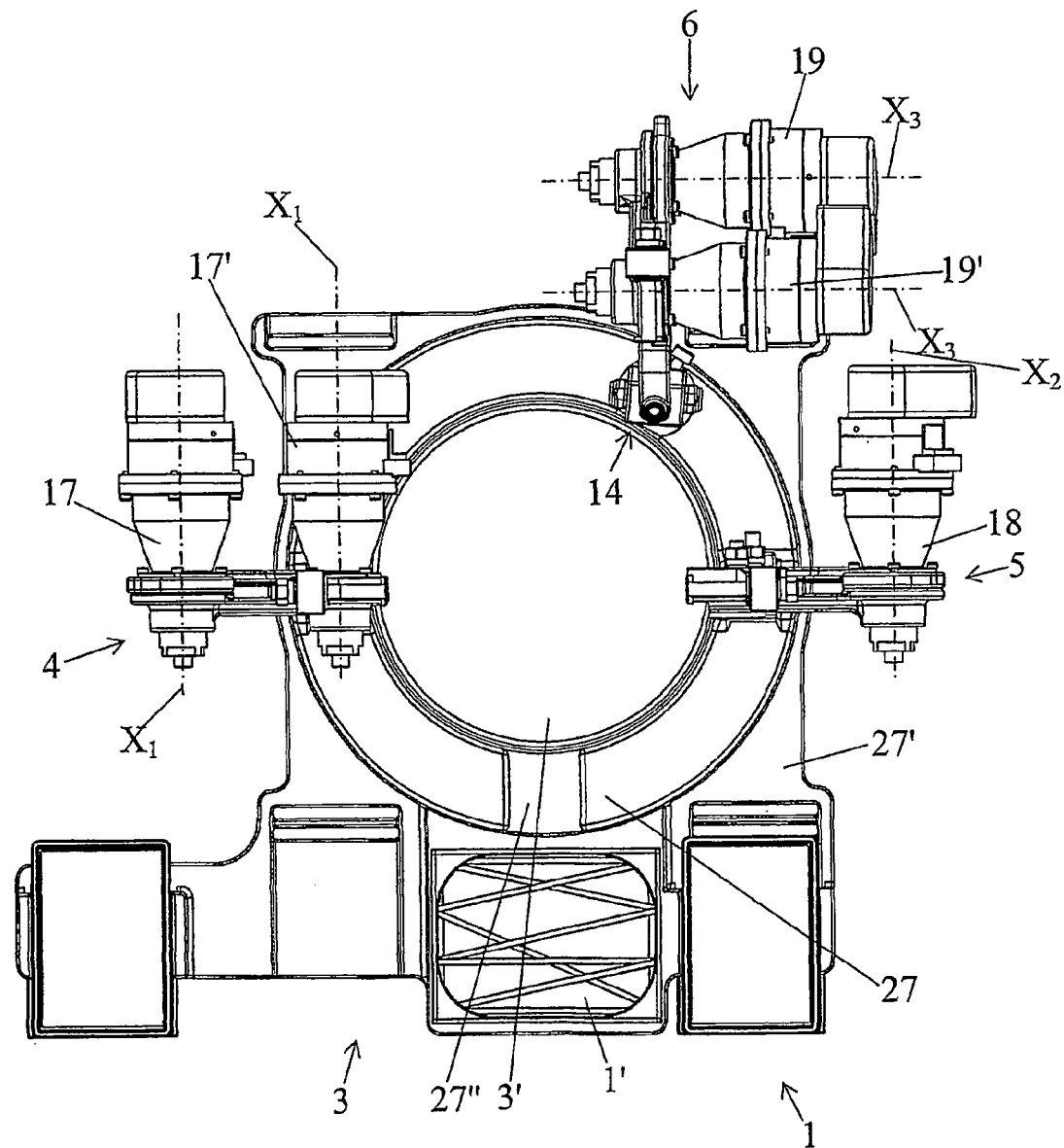
Figure 7:
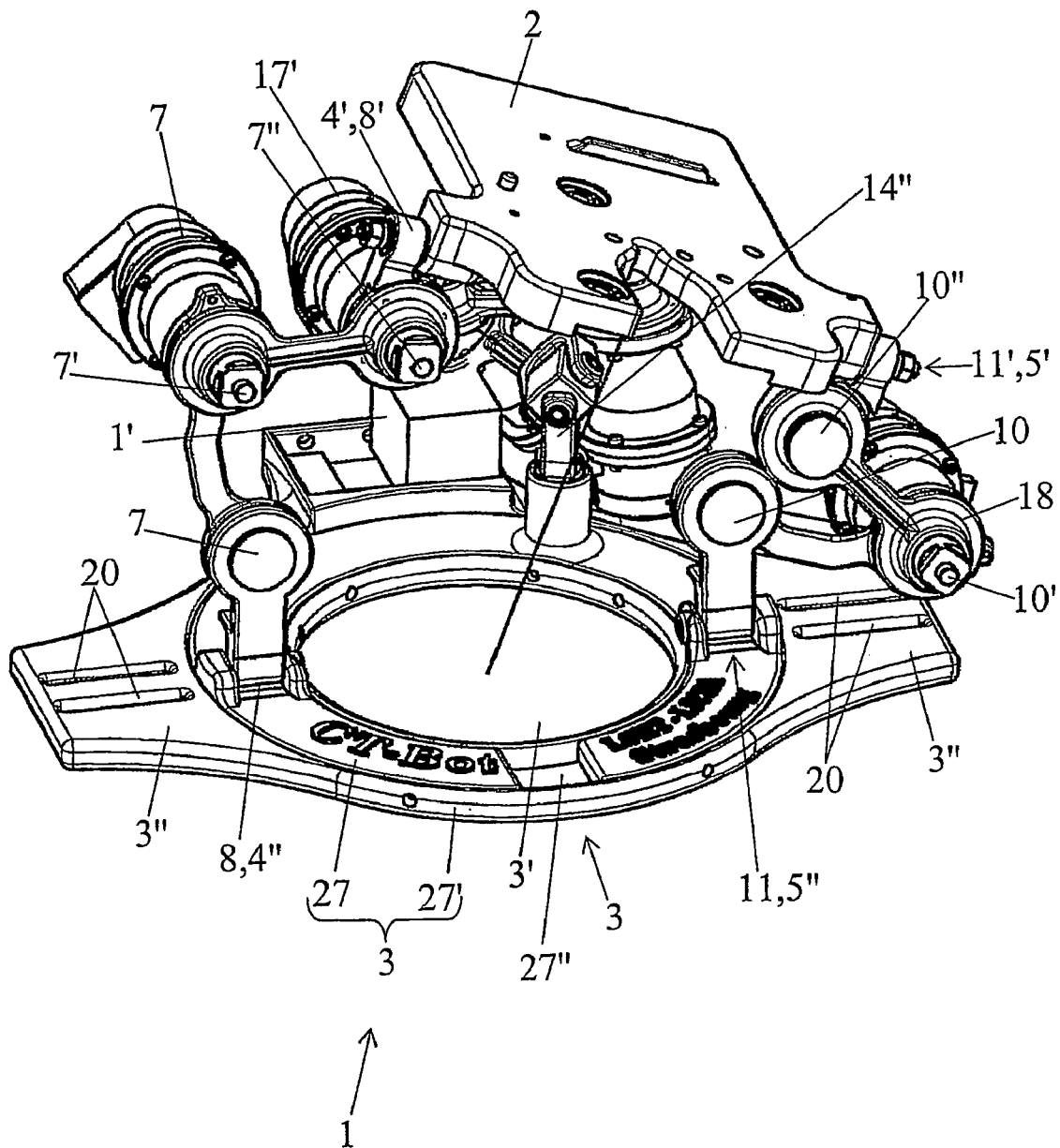
FIGS. 7 to 9 are perspective views of the robotic device according to the invention in three different positions or states (the device of FIG. 7 including a base plate according to an alternate embodiment of the invention)
Figure 8:
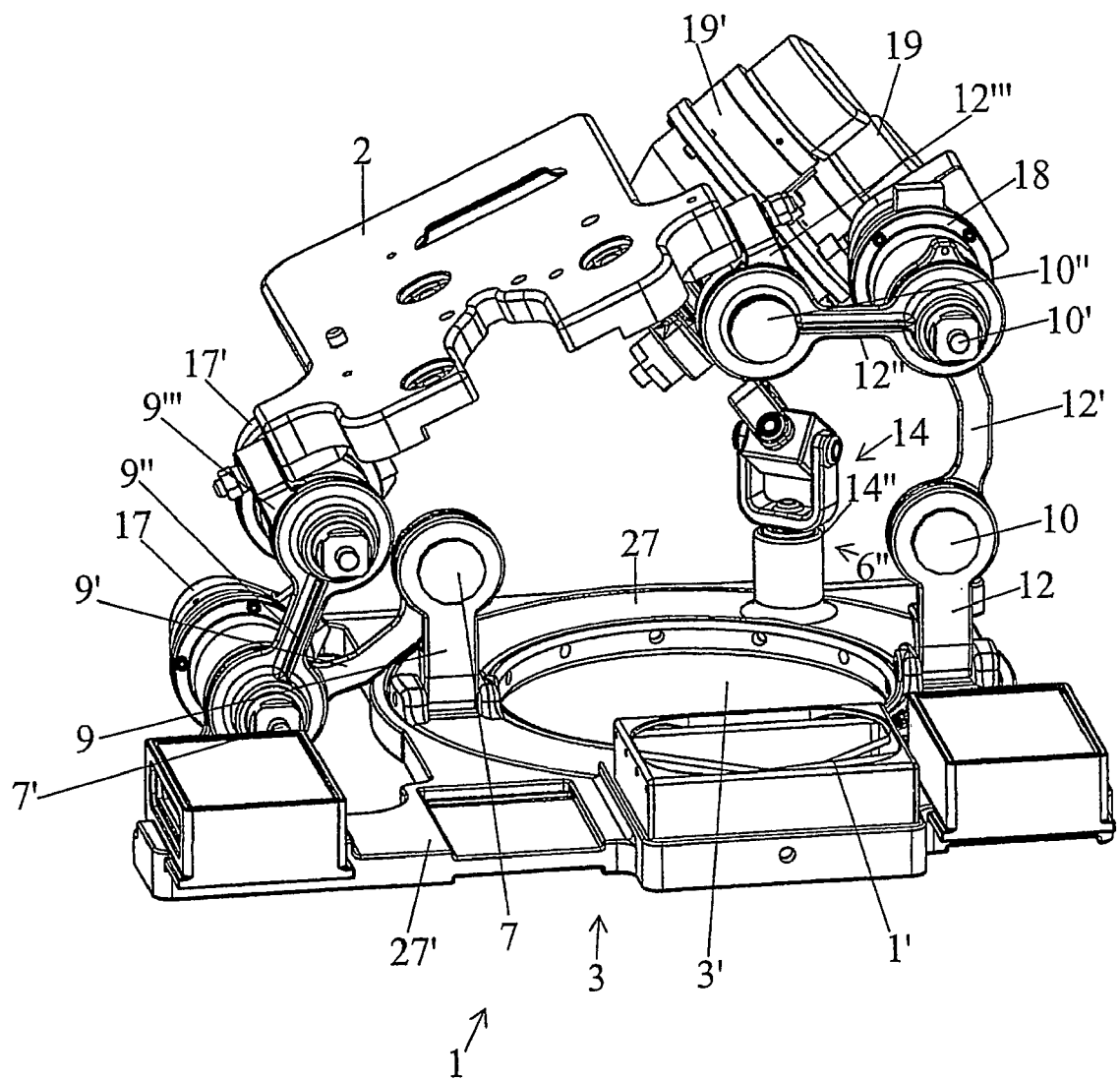
Figure 9:
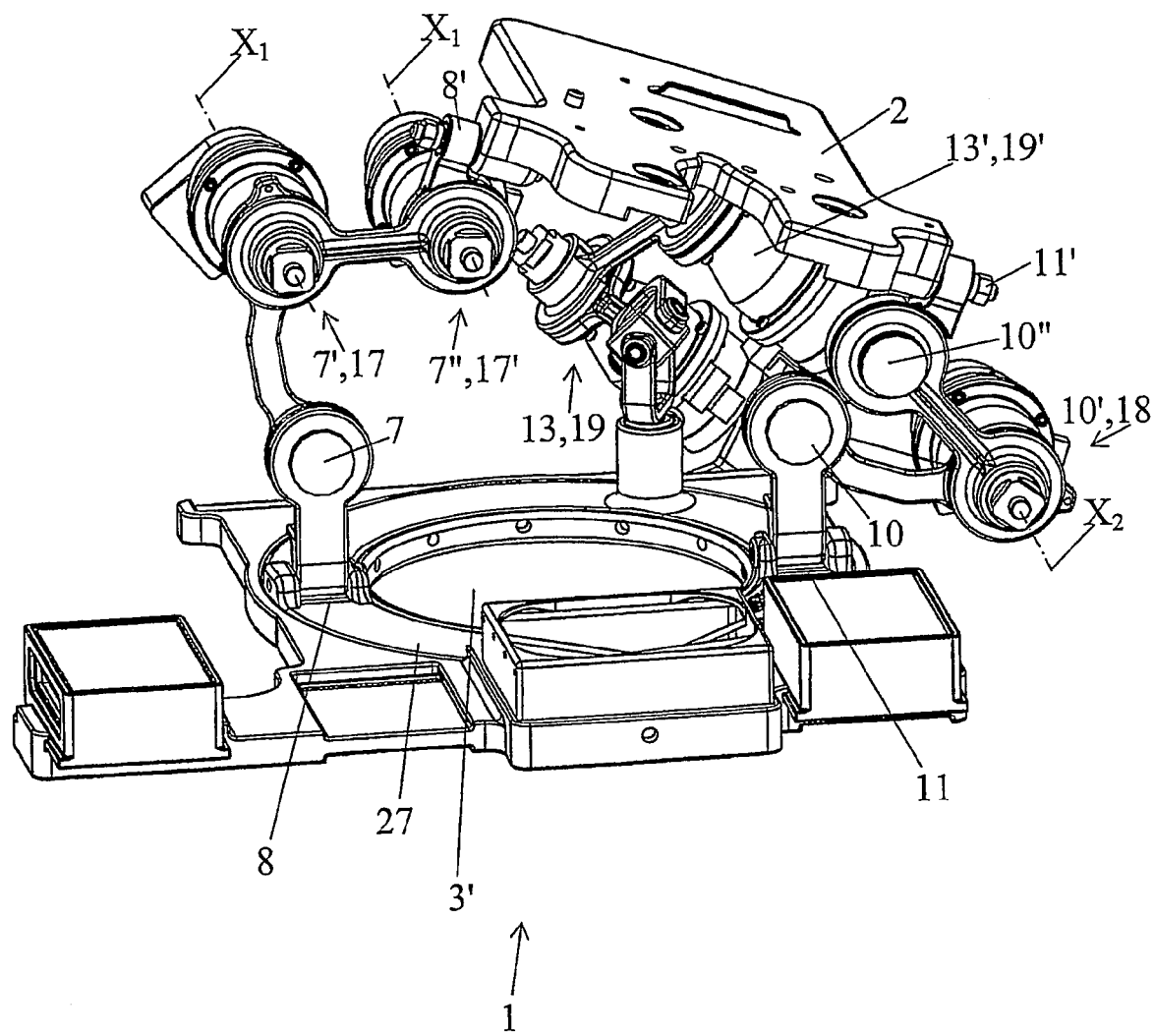
Figure 10:
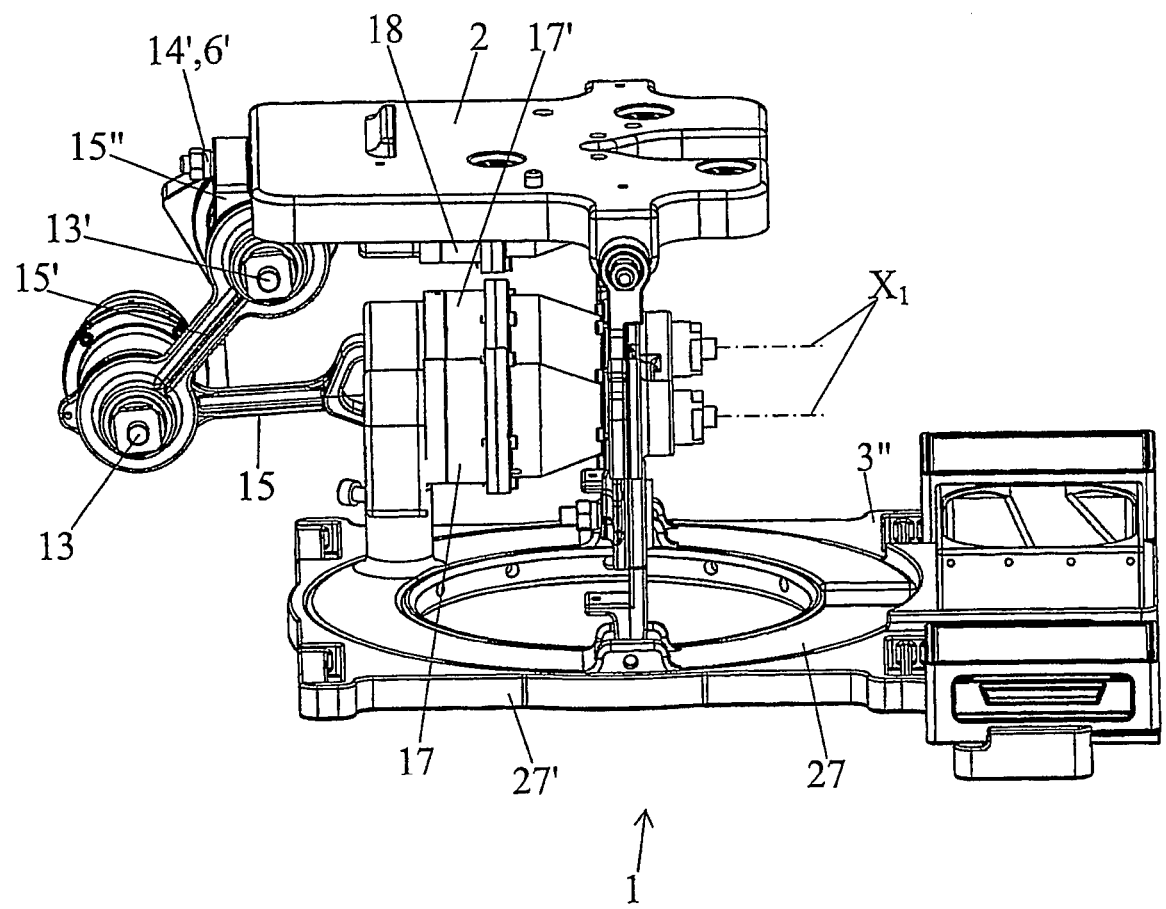
FIGS. 10 to 12 are side prospective views of the robotic device according to the invention in three different positions or states.
Figure 11:
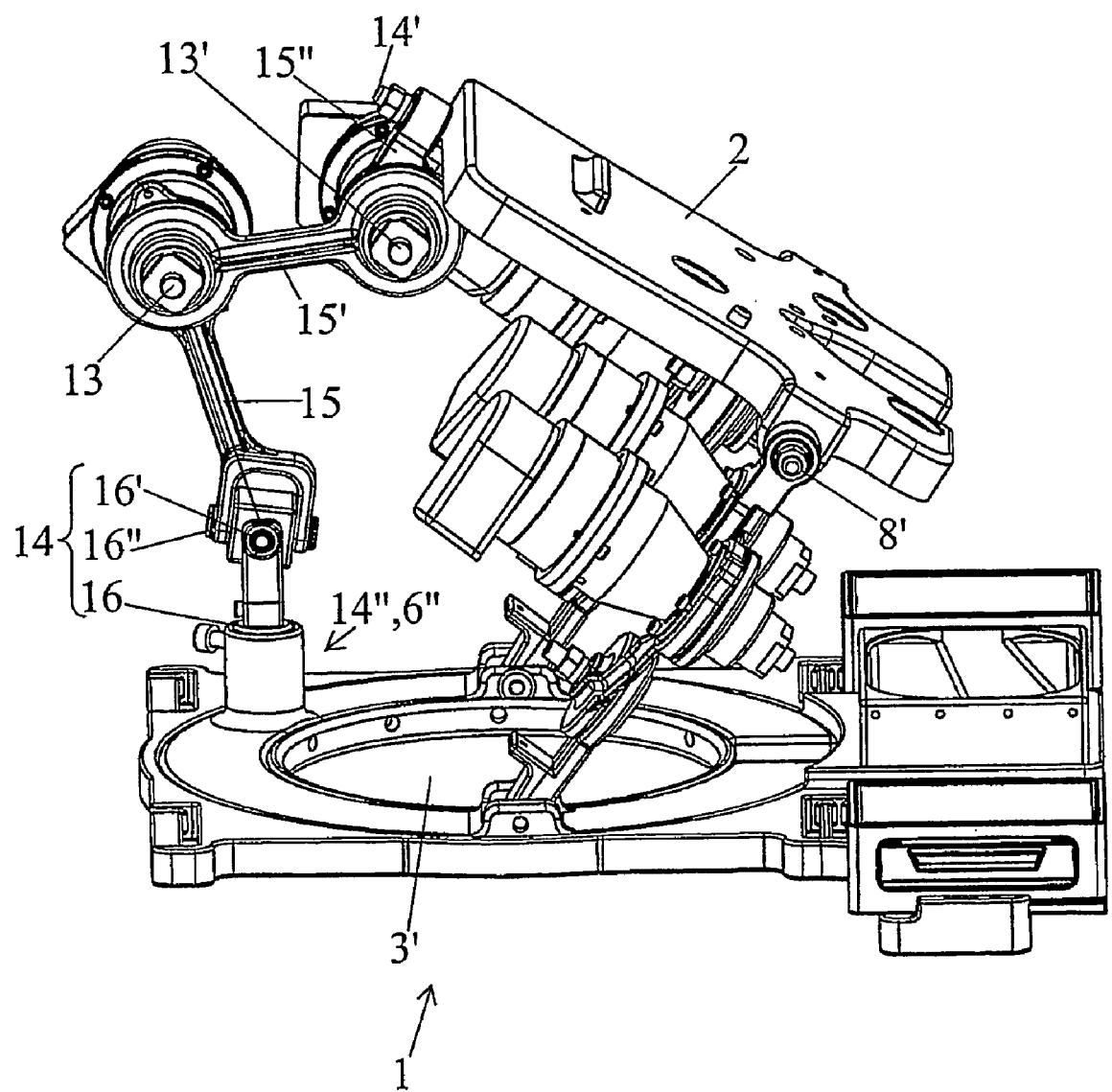
Figure 12:
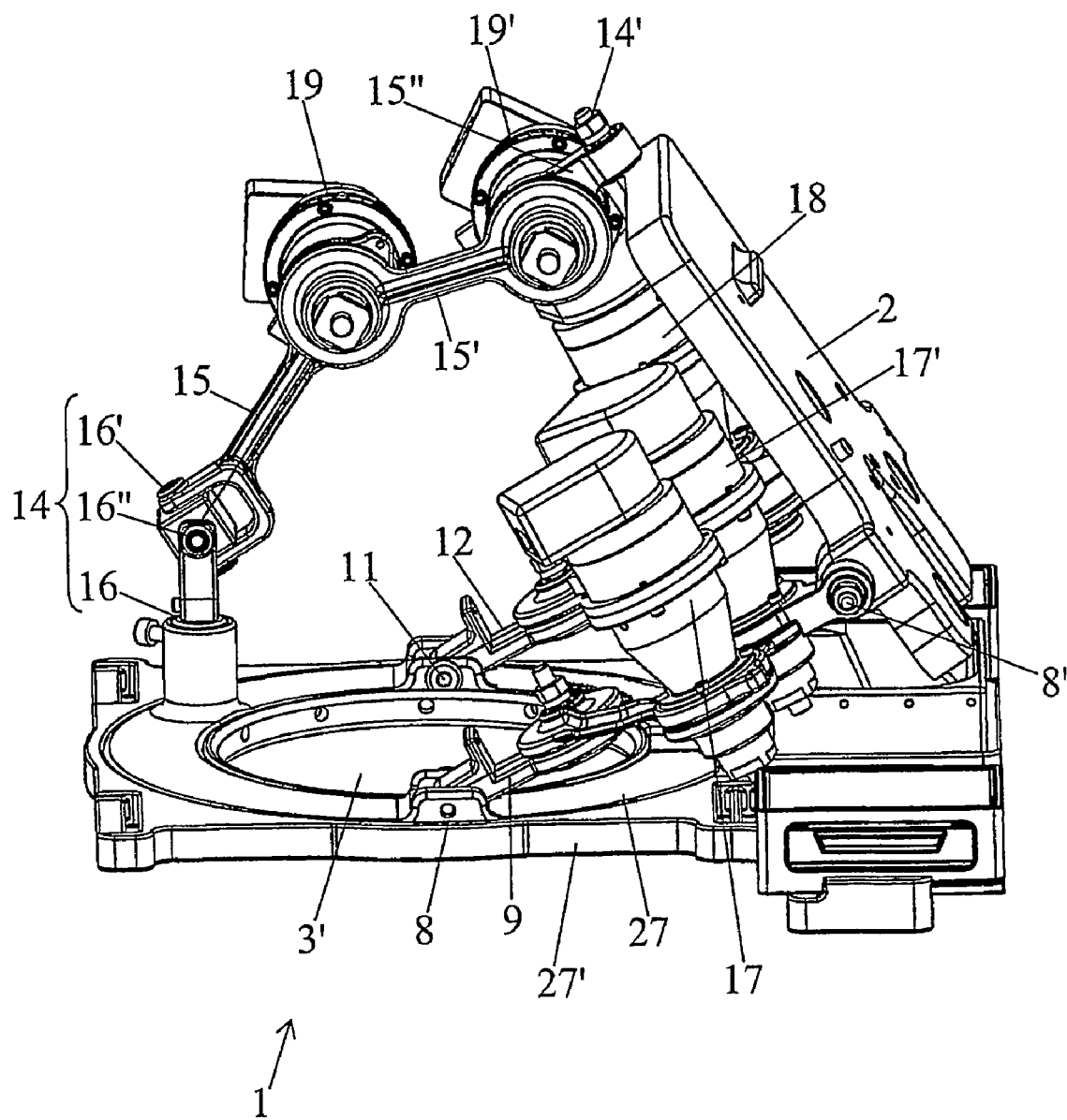
Figure 13:
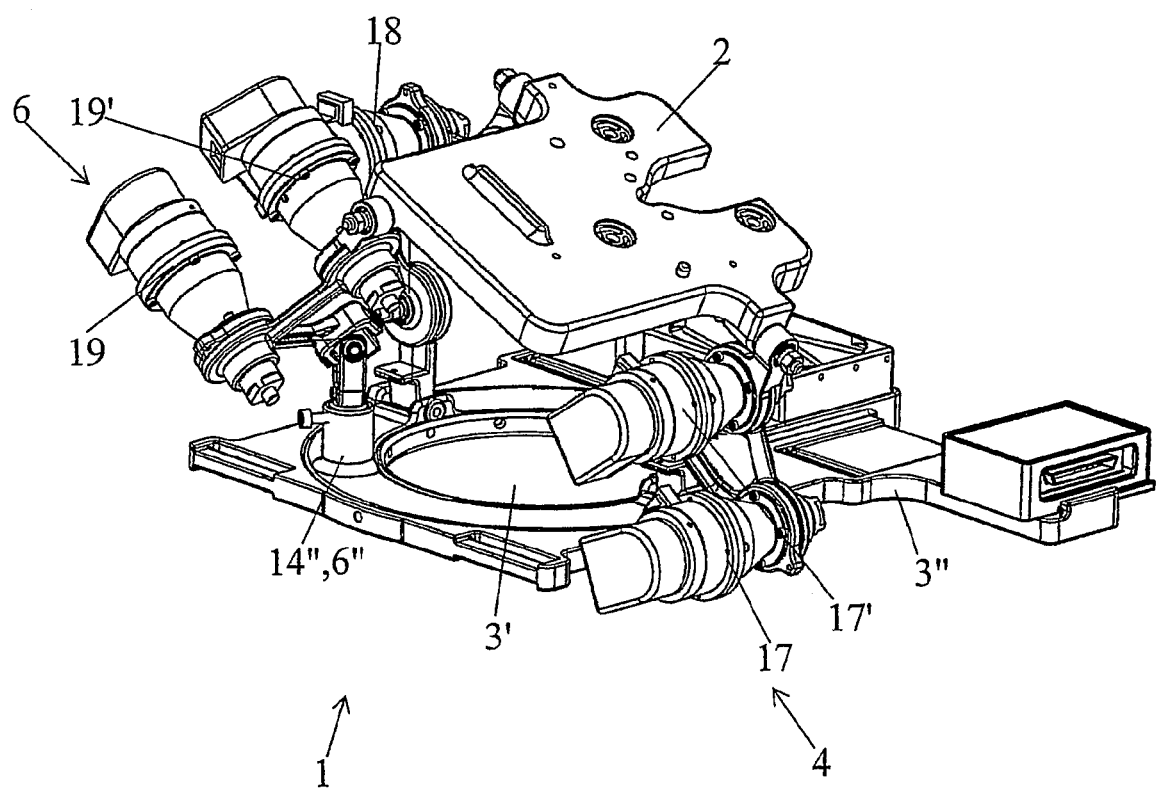
FIGS. 13 to 16 are prospective views of the robotic device according to the invention in four different positions.
Figure 14:
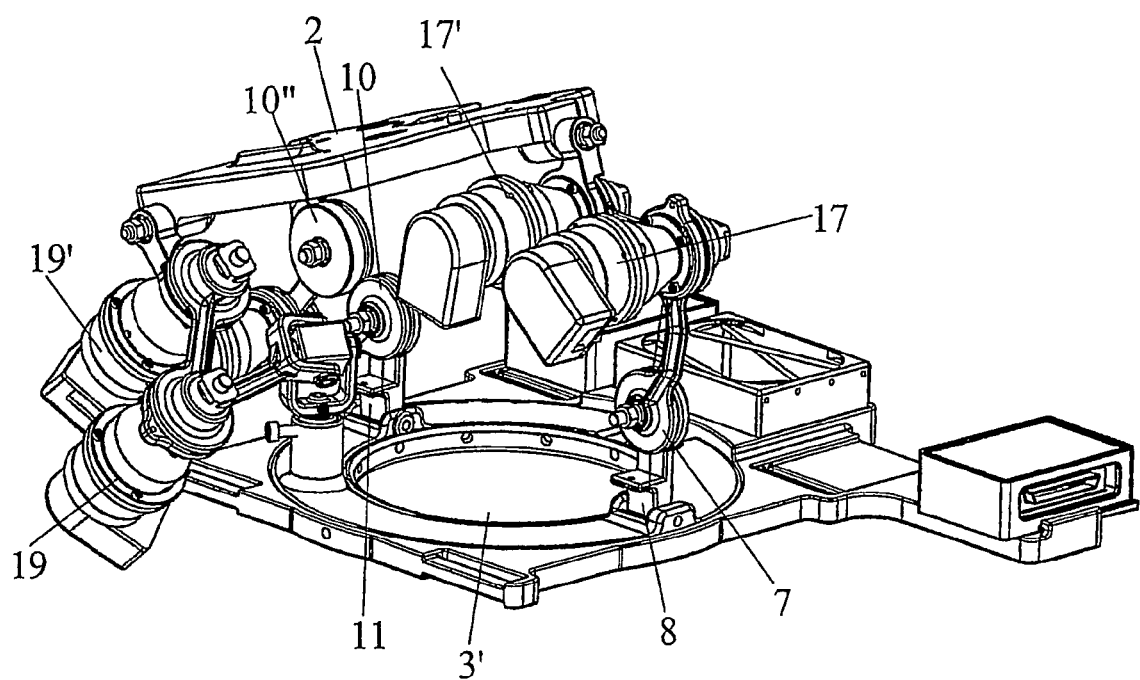
Figure 15:
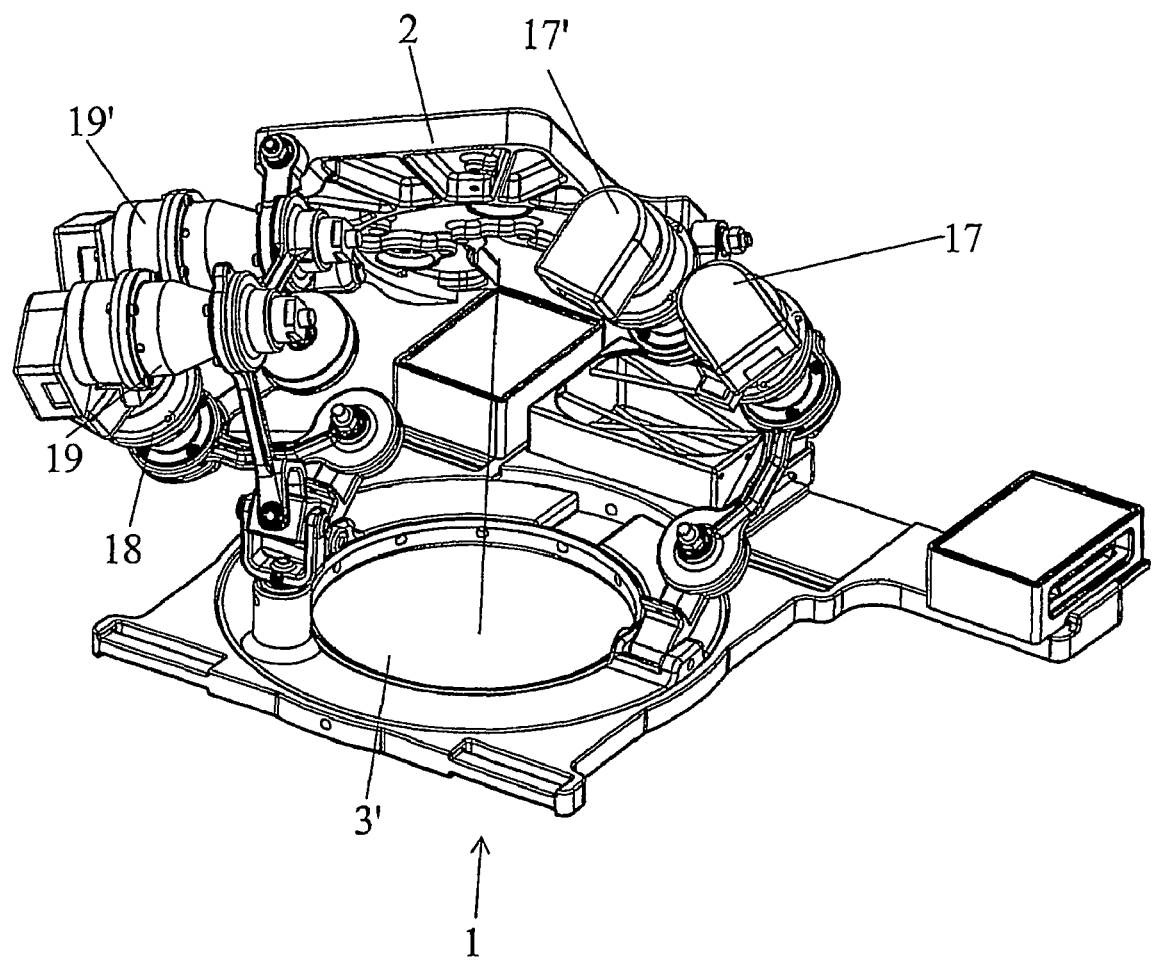
Figure 16:
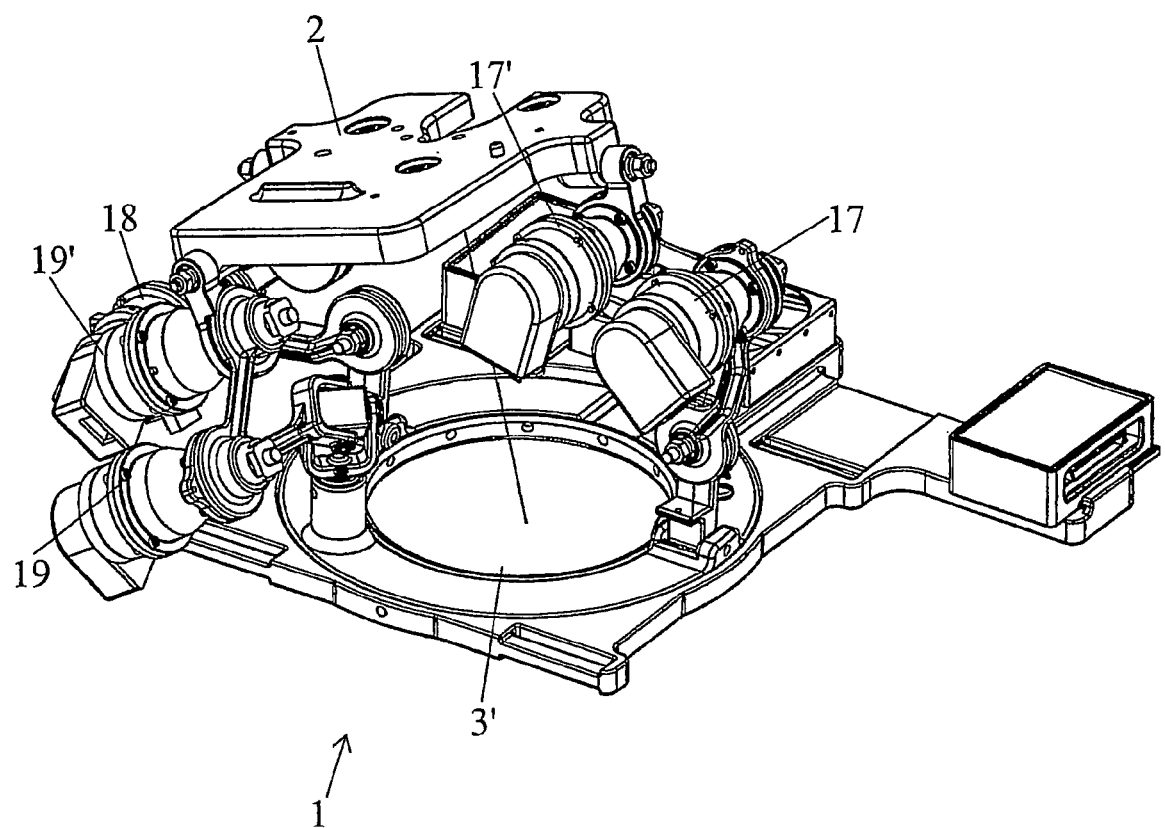
Figure 17:
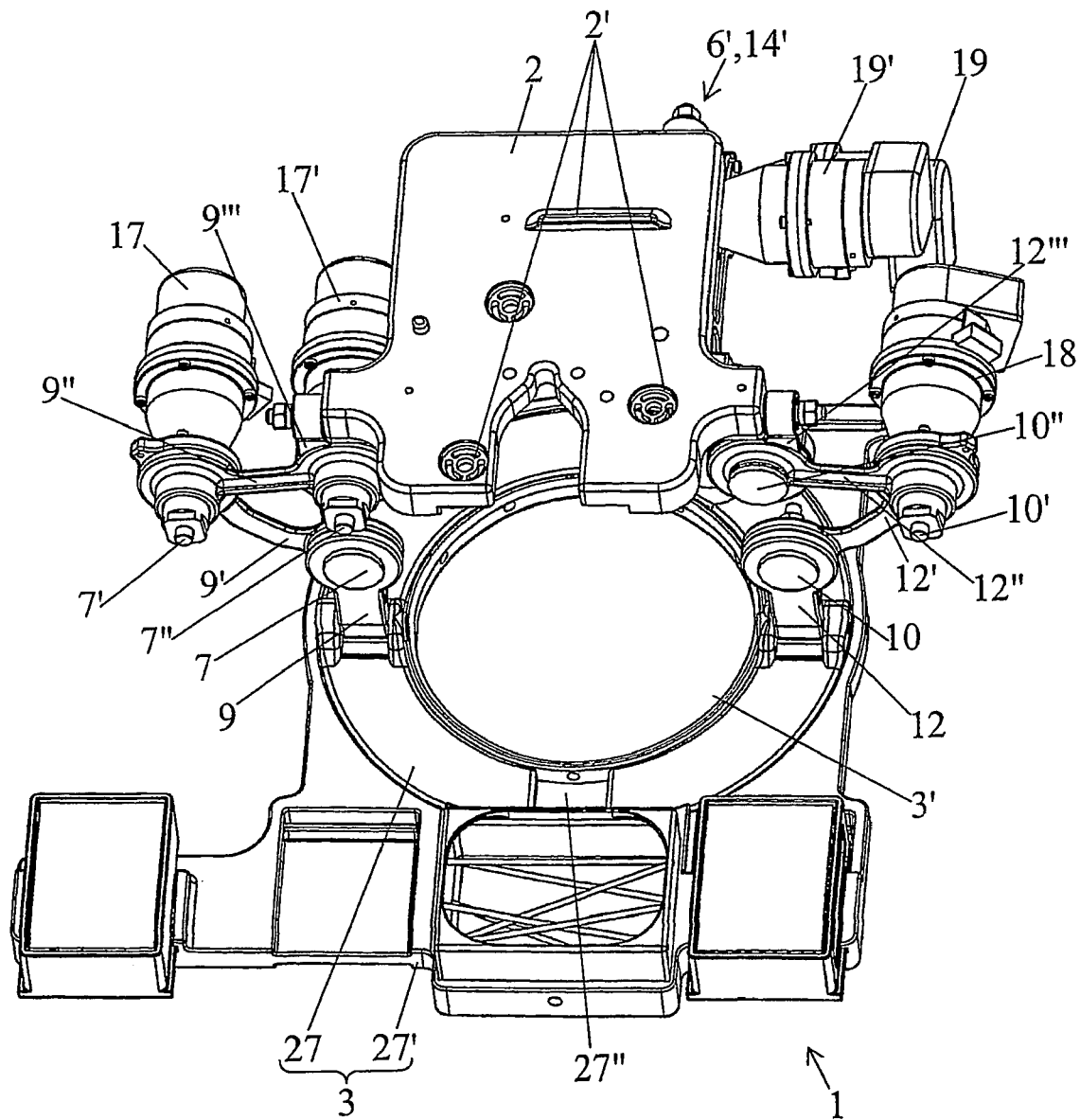
FIGS. 17 and 18 are perspective views from above of the robotic device according to the invention in two different rotational positions.
Figure 18:
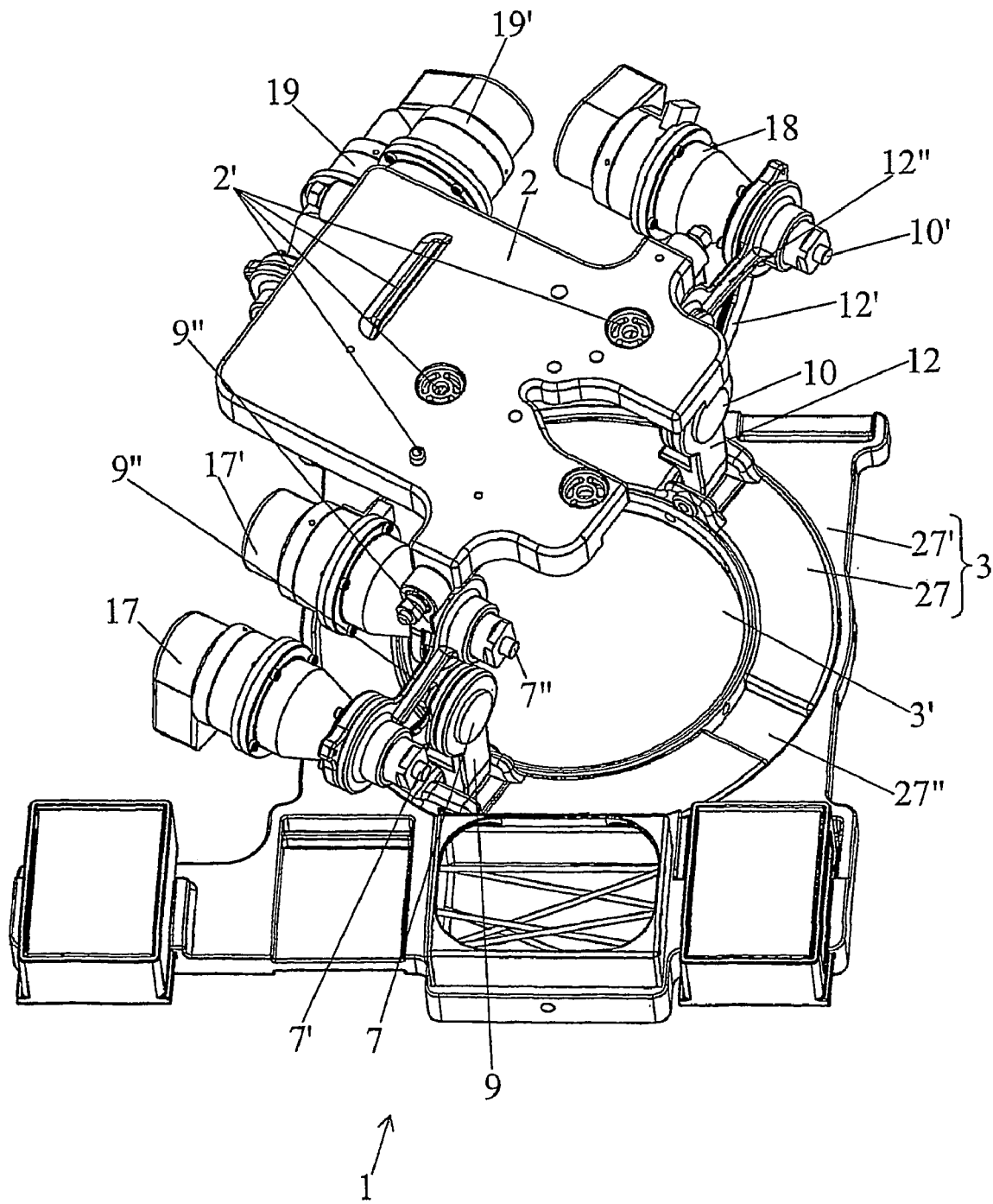
Figure 19:
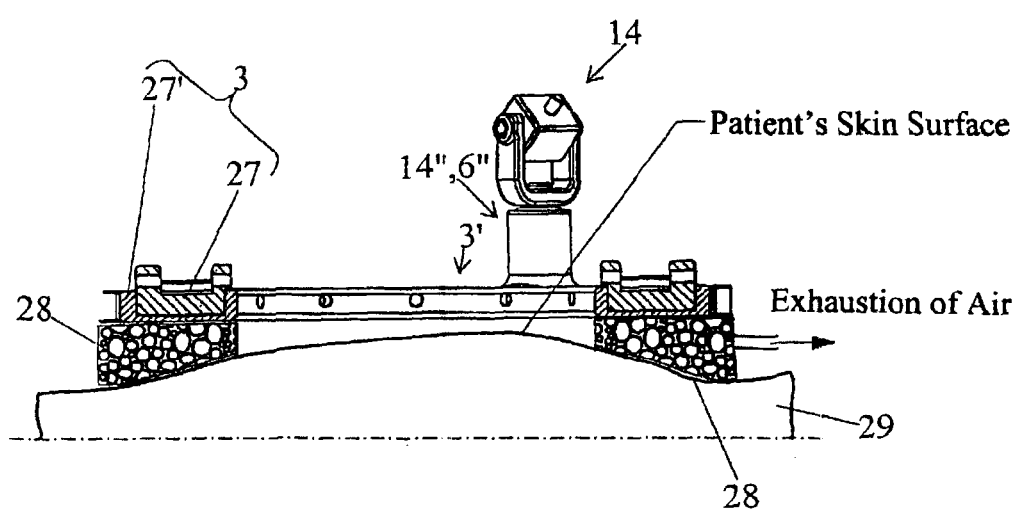
FIG. 19 is a partial cross-sectional view on the level of the base plate of the robotic device according to the invention.

As shown in FIGS. 5 and 19, the padding 28 can for example consist of a flexible annular envelope, fixed under the part 27' of the base plate 3, filled with polystyrene chips and being able to be deformed by aspiration (creation of vacuum) to take a fixed configuration corresponding to that of the bearing surface (skin of the patient).

Figure 21:
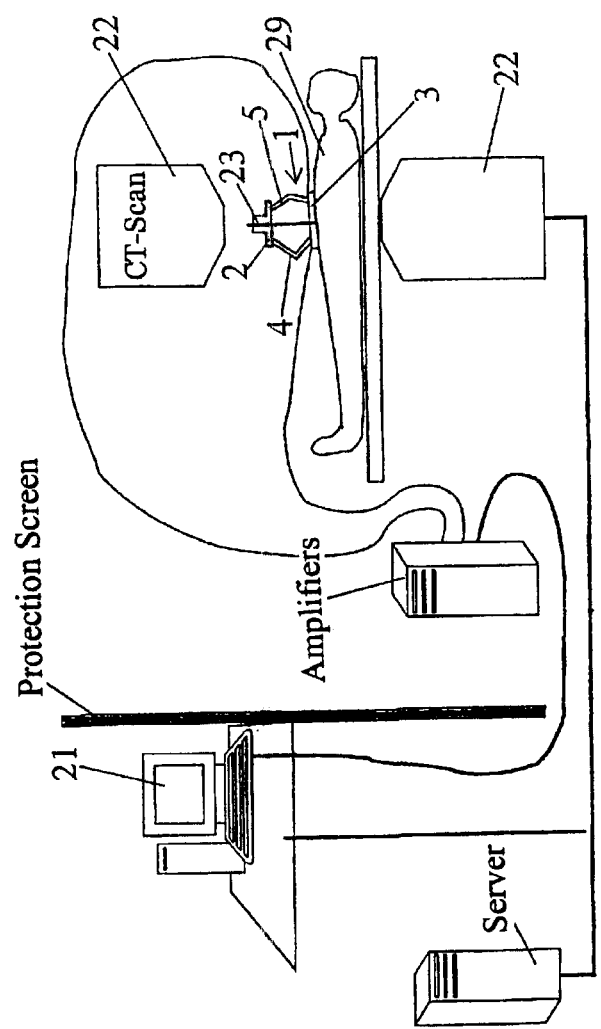

The present invention also concerns, as shown schematically in FIG. 21 of the annexed drawings, a needle carrying apparatus, for the positioning and the controlled depression of a needle in an living subject disposed in a medical imaging apparatus 22, in particular in a cylindrical examination volume of a CT scanner.

This apparatus is characterized in that it is includes a robotic device 1 as described above and a device 23 for retaining optionally with controlled axial displacement, in translation and optionally in rotation, of an injection or biopsy needle, said device 23 for needle retention and displacement being equipped with a means for sensing force in axial direction and being rigidly mounted in an indexed manner on the platform 2 of the robotic device 1.

The device 23 is mounted and attached to the robotic device 1 at the level of the platform 2 and the latter comprises for this purpose of the indexing sites 2', for fixed positioning and adaptive assured mounting, the contact between the two devices 1 and 23 being preferably of a surface nature.

These two devices are controlled by an operation and control data-processing unit 21, in correlation with receptions from recorded displays and/or receptions in real time from a medical imaging apparatus 22 and in co-operation preferably with a servomotor and amplifier means.

The control unit 21 and its display means are located remotely from the imaging apparatus 22, preferably behind a protective screen.

Such an apparatus is described more in detail in the two following publications:

"Needle tip positioning on the abdomen with a novel stereotaxic robotic assistant", B Maurin et al., Computer-Aided Medical Interventions: tools and applications, Conference SURGETICA, Chambéry, France, January 2005.

"A parallel robotic System with force sensors for percutaneous procedures under CT-guidance" (A parallel robotic system with sensors of force for percutaneous procedures under CT-guidance), Benjamin Maurin et al., Medical Image Computing and Computer-Assisted Intervention—MICCAI 2004, pages 176-183, Saint-Malo, France, October 2004.

The contents of these two publications are incorporated entirely in present description by reference.

Of course, the invention is not limited to the embodiments described and represented in the annexed drawings. Modifications remain possible, in particular from the point of view of the constitution of the various elements or by substitution of technical equivalents, without leaving for all that the field protection of the inventions.

The invention claimed is:

1. A robotic device for positioning and orientating a platform having a coordinate system ($O_f$, $x_f$, $y_f$, $z_f$) and being movable relative to a base having a coordinate system ($O_0$, $x_0$, $y_0$, $z_0$) the platform being located displaced from the base and being connected to the latter by first, second and third articulated leg structures forming three parallel mechanical connections, of which each one includes a series of leg segments connected to each other, in pairs, by pivoting joints each one having at least one pivoting axis, the opposite end portions of each of the three leg structures being connected by joints each having at least one pivot axis with the platform and with the base in predetermined connection points, wherein:

the respective pivot axes of the pivoting joints of the first and second leg structures with the platform and the base are configured to define a first common axis of rotation ($\Delta_1$) between the base and the two opposite leg structures and a second common axis of rotation ($\Delta_2$) between the two opposite leg structures and the platform, said common pivot axes ($\Delta_1$ and $\Delta_2$) are coplanar in a first plane, pivot axes ($X_1$; $X_2$) of the pivoting joints connecting the leg segments of the first and second leg structures are all parallel between each other and perpendicular to a second plane, the first and second planes are not mutually perpendicular, the third articulated leg structure is connected, in an articulated manner, with the platform in a connection point not aligned with the connection points of the first and second leg structures with said platform and with the base in a connection point not aligned with the connection points the first and second leg structures with said base, parallel rotary joints provided by the first, second, and third leg structures permit a controlled determination of a position of the origin ($O_f$) of the coordinate system ($O_f$, $x_f$, $y_f$, $z_f$) assigned to the platform and the orientation the platform coordinate system ($O_f$, $x_f$, $y_f$, $z_f$) relative to the coordinate system ($O_0$, $x_0$, $y_0$, $z_0$) assigned to the base, such that at least five degrees of freedom are provided.

2. The robotic device according to claim 1, wherein each the first and second leg structures is composed of four leg segments assembled in series, successively from a first to a fourth, and connected to each other, in pairs, by three pivoting joints around axes (X1; X2) perpendicular to the second plane.

3. The robotic device according to claim 1, wherein each of the first and second leg structures is composed of three leg segments assembled in series, successively from first to a third, and connected to each other, in pairs, by two joints pivoting around axes (Xl; X2) perpendicular to the second plane and in that the leg segments include telescopic segments.

4. The robotic device according to claim 2, wherein the planes are common.

5. The robotic device according to claim 1, wherein the first and second leg structures constitute structures of opposite and symmetrical legs, with pivoting joints respectively located in a symmetrical manner and the leg segments are respectively of identical form, the longitudinal axes of all the above mentioned leg segments, or at least axes of the mechanical connections respectively provided by the latter, being located in at least one of the first plane, the second plane and a plane parallel with the one of the first and second planes.

6. The robotic device according to claim 2, wherein a first of the two opposite leg structures comprises two pivoting joints with regulated and controlled movements and the second of the two opposite leg structures has a single pivoting joint with controlled and regulated movement.

7. The robotic device according to claim 3, wherein the two telescopic segments are adjustable in length in a controlled way, and one of the pivoting joints of the one of the first and second leg structures is regulated and controlled in movement.

8. The robotic device according to claim 6, wherein two mechanical and parallel kinematics connections formed by the first and second opposite leg structures connecting the base to the platform include three controlled parameters for the first leg structure, a distance between the axis of a first of the pivoting joints connecting the first and the second leg segments and the axis of a second of the pivoting joints connecting the third and fourth leg segments and an angle ($\alpha$) between a straight line connecting said first and second pivoting joints and defining the length and a straight line connecting the first and second pivoting joint of the first leg structure to the corresponding joint of the second leg structure, and for the second leg structure, a distance between the axis of the joint connecting the first and the second of the leg segments and the axis to the joint connecting the third and the fourth leg segments.

9. The robotic device according to claim 1, wherein the connection point of the third leg structure with the platform is located apart from a median plane ($O_f$, $x_f$, $z_f$) of the two connection points of the first and second leg structures with said platform, perpendicular to the axis of rotation ($\Delta_2$) between first and second let structures and the platform, and in that the connection point of the third leg structure with the base is located apart from a median plane ($O_0$, $x_0$, $z_0$) of the two connection points of the first and second leg structures with said base, perpendicular to the axis of rotation ($\Delta_1$) between the first and second leg structures and the base.

10. The robotic device according to claim 1, wherein the third leg structure is composed of three leg segments assembled in series successively from a first to a third, and connected to each other, in pairs, by two pivoting joints around axes parallel to each other.

11. The robotic device according to claim 9, wherein the third leg structure is composed of two leg segments connected to each other by a pivoting joint around an axis and one of the two leg segments is telescopic.

12. The robotic device according to claim 10, wherein the longitudinal axes of the leg segments are located in one or more planes perpendicular to the pivot axis or axes.

13. The robotic device according to claim 6, wherein the opposite end leg segments of the third leg structure are, each one, connected by a non-driven joint respectively to the base and the platform, and the joint connecting the first segment to the base is of a knee type and in that the joint connecting the third segment to the platform is of a type pivoting around an axis perpendicular to the pivot axis ($\Delta_2$) between the first and second leg structures and the platform.

14. The robotic device according to claim 10, wherein a mechanical and kinematic connection formed by the third leg structure includes two controlled parameters, namely, a distance between a center of a free rotation of the knee joint and the axis of the pivoting joint connecting the first and the second leg segments or the second and the third leg segments and the angle ($\beta$) between a first straight line connecting the first segment to base pivoting joint and the first leg segment to second leg segment pivoting joint and a straight line contained in a plane containing said straight line defining the distance and parallel to the plane(s) containing longitudinal axes of the leg segments and/or of the corresponding mechanical connections connecting the axis of said first leg segment to second leg segment pivoting joint to the straight line connecting the pivoting joints of the first and second leg structures.

15. The robotic device according to claim 10, wherein the two pivoting joints connecting the leg segments are both driven and controlled in movement.

16. The robotic device according to claim 11, wherein one of the pivoting joints connecting the leg segments is driven and controlled in movement and that a telescopic one of the leg segments is adjustable in length in a controlled manner.

17. The robotic device according to claim 13, wherein the joint of the knee type includes three pivoting or rotating joints in juxtaposed association comprising axes of concurrent rotation.

18. The robotic device according to claim 6, further including actuators for driving and controlling respective movements of the joints which drive and control movement of the three leg structures include at least one of piezoelectric and ultrasonic drives.

19. The robotic device according to claim 7, wherein the telescopic leg segments include at least one of electric and piezoelectric extendable cylinders and the pivoting joints that are driven and controlled in movement and include at least one of piezoelectric and ultrasonic drives.

20. The robotic device according to claim 18, wherein each drive includes at least one of an ultrasonic motor and a piezoelectric motor associated with a reducer and an incremental encoder, each one of these drives being mounted in a corresponding casing and controlled in accordance with each other by a central operation and control processing unit which collects the data delivered by the encoders.

21. The robotic device according to claim 1, wherein the leg segments as well as the platform and the base are made out of a rigid material and compatible with x-ray medical imaging procedures, and the pivoting joints of the three leg structures include at least one of sleeves and annular bearings.

22. The robotic device according to claim 1, further including a spatial reference and multi-axial indexing part.

23. The robotic device according to claim 1, wherein the platform comprises one or more mounting and attaching sites for a device for retention and axial displacement and controlled depression of at least one of a needle, an elongated object, a device for producing a jet, and a device for producing a rectilinear beam and the base presents an appreciably annular form with a central opening located under the platform and with side extensions forming a support structure.

24. The robotic device according to claim 1, wherein the base is provided with an attachment structure, for assured mounting of the device on the abdomen of a subject.

25. The robotic device according to claim 1, wherein the base is made of two assembled parts in a removable manner with rotational indexing around a central opening including a first part in a shape of a ring connected to the leg structures and a second part delimiting the central opening, integral with side extensions of the base and comprising, around said opening, a circular groove for the reception of the first annular part.

26. The robotic device according to claim 1, wherein the base has a covering adapted to conform with a body on which it is supported.

27. A needle-carrying apparatus, for positioning and controlled depression of a needle in an alive subject disposed in a medical imaging apparatus comprising:
 a robotic device according to claim 1; and
 a needle carrying device for retaining and controlling axial displacement of a needle, said retaining device being equipped with at least a sensor of force acting in an axial direction and being mounted rigidly on the platform of the robotic device, the needle carrying device and the robotic device being controlled by a data-processing unit, in correlation with views taken by a medical imaging scanner.

28. The robotic device according to claim 7, wherein two mechanical and parallel kinematics connections formed by the first and second opposite leg structures connecting the base to the platform include three controlled parameters, namely, for the first of the two leg structures, a distance between the axis of the pivoting joint connecting the first and the second leg segments and the axis of the pivoting joint connecting the third and fourth leg segments, and, angle ($\beta$) between a straight line connecting said two joints and defining the length and the straight line connecting the last of the above mentioned joints of the first leg structure to the corresponding joint of the second leg structure, and for the second of the two leg structures, a distance between the axis of the joint connecting the first and the second of the leg segments and the axis to the joint connecting the third and the fourth leg segments.

29. The robotic device according to claim 11, wherein the longitudinal axes of the leg segments are located in one or more planes perpendicular to the one or more pivot axes.

30. The robotic device according to claim 14, wherein the joint of the knee type includes three pivoting or rotating joints in juxtaposed association comprising axes of concurrent rotation.

31. The robotic device according to claim 15 further including actuators for driving and controlling respective movements of the joints which drive and control movement of the three leg structures include at least one of piezoelectric and ultrasonic drives.

32. The robotic device according to claim 16, wherein the telescopic leg segments include at least one of electric and piezoelectric extendable cylinders and the pivoting joints that are driven and controlled in movement and include at least one of piezoelectric and ultrasonic drives.

* * * * *